(12) United States Patent
Kim et al.

(10) Patent No.: US 9,512,492 B2
(45) Date of Patent: Dec. 6, 2016

(54) METHOD OF MANUFACTURING REFERENCE MATERIAL USING PLANT CULTURED CELL LINES

(75) Inventors: Hyong Ha Kim, Daejeon (KR); Woo Jeong Kim, Daejeon (KR); Jung Keun Suh, Seoul (KR)

(73) Assignee: KOREA RESEARCH INSTITUTE OF STANDARDS AND SCIENCE (KR)

( * ) Notice: Subject to any disclaimer, the term of this patent is extended or adjusted under 35 U.S.C. 154(b) by 484 days.

(21) Appl. No.: 13/513,096

(22) PCT Filed: Dec. 16, 2010

(86) PCT No.: PCT/KR2010/009027
§ 371 (c)(1),
(2), (4) Date: Jul. 19, 2012

(87) PCT Pub. No.: WO2011/074897
PCT Pub. Date: Jun. 23, 2011

(65) Prior Publication Data
US 2012/0282620 A1 Nov. 8, 2012

(30) Foreign Application Priority Data
Dec. 16, 2010 (KR) .................. 10-2010-0128970

(51) Int. Cl.
*C12Q 1/68* (2006.01)
*G01N 33/50* (2006.01)

(52) U.S. Cl.
CPC ......... *C12Q 1/6895* (2013.01); *G01N 33/5097* (2013.01)

(58) Field of Classification Search
None
See application file for complete search history.

(56) References Cited

FOREIGN PATENT DOCUMENTS

| KR | 10-2003-0084174 | | 11/2003 |
|---|---|---|---|
| KR | 2003-0084184 | * | 11/2003 |
| KR | 10-0439168 | | 7/2004 |
| KR | 10-0687765 | | 3/2007 |
| KR | 10-0707830 | * | 4/2007 |

OTHER PUBLICATIONS

Taylor et al. (1995) Theor Appl Genet vol. 90: 1169-1173.*
Holst-Jensen et al. (2003) Anal. Bioannal Chem vol. 375:pp. 985-993.*
Gisbert et al. (2003) Biochemical and Biophysical research commuication 303: pp. 440-445.*
English Translation of the International Search Report for International application No. PCT/KR2010/009027 mailed Sep. 14, 2011.

* cited by examiner

*Primary Examiner* — Suchira Pande
(74) *Attorney, Agent, or Firm* — Swanson & Bratschun, L.L.C.

(57) ABSTRACT

A method of manufacturing a reference material for determining incorporation of a genetically modified (GM) plant into a sample or analyzing a mixing ratio from a tissue-cultured cell line that is obtained by incubating tissues of either a GM plant or a non-GM plant, and a method of determining incorporation of a GM plant into a sample and analyzing a mixing ratio using the reference material are provided. The reference material for determining the incorporation of a genetically modified (GM) plant a sample or analyzing a mixing ratio using the tissue-cultured cell lines that are obtained by incubating tissues of the GM plant and the non-GM plant can be useful in producing a countless number of populations having the same genetic traits via the tissue culture. Thus, when a culture capacity of the reference material is increased to a large volume, it is possible to obtain a large volume of the reference material having uniform qualities with no quality variation between batches. Unlike the conventional reference materials manufactured using grain powder, a reference material with 100% purity can be obtained as either a GM or non-GM reference material by verifying the purity of the tissue-cultured cell line. Accordingly, it is possible to provide the uniform and stable supply of a reference material having uniform compositions.

5 Claims, 6 Drawing Sheets

METHOD OF MANUFACTURING REFERENCE MATERIAL USING PLANT CULTURED CELL LINES

CROSS-REFERENCE TO RELATED APPLICATION

This application is a 35 U.S.C. §371 national phase application of PCT/KR2010/009027 (WO 2011/074897), filed on Dec. 16, 2010, entitled " METHOD OF MANUFACTURING REFERENCE MATERIAL USING PLANT CULTURED CELL LINES", which application claims priorities to and the benefits of Korean Patent Application No. 2009-0126139, filed on Dec. 17, 2009 and Korean Patent Application No. 2010-0128970, filed on Dec. 16, 2010, the disclosure of which are incorporated herein by reference in its entirety.

BACKGROUND

1. Field of the Invention

The present invention relates to a method of manufacturing a reference material for determining incorporation of a genetically modified (GM) plant into a sample or analyzing a mixing ratio from a tissue-cultured cell line that is obtained by incubating tissues of either a GM plant or a non-GM plant, and a method of determining incorporation of a GM plant into a sample and analyzing a mixing ratio using the reference material.

2. Discussion of Related Art

A genetically modified organism (GMO) refers to an organism whose productivity or functionality is improved by artificially separating genes of interest from animals, plants or microorganisms and binding the separated genes, unlike the development of a breed using a conventional plant breeding technique. In general, genes associated with herbicide resistance, insect tolerance, disease tolerance, cold resistance and/or nutrition supplement are introduced into a plant so as to improve the productivity of GMOs and enhance the quality of the GMOs.

Examples of GMOs which are the most commercially available all over the world include maize and beans. In addition, this genetic engineering technique may apply to other crops such as cotton, canola, potatoes and tomatoes. However, since the safety of GMOs is not scientifically verified, a labeling system in which a plant is labeled as a GMO when at least 3% of the GMO is mixed with its original plant is currently being enforced in Korea. Although there is a difference in threshold in other countries, similar labeling systems are in effect.

Therefore, a technique of quantitatively determining a mixing ratio is required in addition to a qualitative analysis method of detecting an incorporated GMO.

The quantitative analysis of GMOs is mainly divided into two categories: a protein analysis method and a DNA analysis method. In general, an ELISA method using a protein expressed from a gene introduced into a GMO has problems in that a detection rate is inferior to that of a PCR method, and proteins may be denatured due to heat treatment. Therefore, a technique for quantifying a gene that is introduced into a GMO using a real-time PCR method has been widely used. In order to quantify a mixing ratio in a GMO sample using the real-time PCR method, a reference material which can compare the copy number of a gene introduced into the GM plant is required.

As the GMO labeling system has come into effect, the accuracy and precision of analysis of the incorporation threshold at which a GMO is incorporated into a sample are very important, and a reference material used for the analysis is the most important so as to analyze the incorporation threshold with accuracy and precision. The reference material has to have secured long-term storage opportunities and show its own stability and homogeneity as well.

In recent years, a reference material prepared by mixing ground seed powder of a GMO and a non-GMO derived from respective crops at a certain weight ratio based on a conventional method, or a standard plasmid prepared by inserting an amplicon containing an endogenous gene and an inserted gene, which is extracted from a sample in which the GMO and the non-GMO are mixed at a certain weight ratio, has been used as the reference material. However, the reliability of these reference materials remains to be improved. In particular, lack of information on the purity of a starting sample and technology for proving the information is blocking the manufacture of the reference material. Therefore, a more stably and uniformly available reference material is required.

SUMMARY OF THE INVENTION

The present invention aims to improve the reliability of a reference material so as to secure or verify the purity of the starting sample. Thus, the present invention is directed to providing a method of manufacturing a reference material for analyzing a mixing ratio of a GM plant in a sample, wherein the purity of a starting sample is completely verified and the homogeneity of the starting sample is also secured, and a method of analyzing a mixing ratio of a GM plant in a sample using the reference material.

One aspect of the present invention provides a method of manufacturing a reference material for determining incorporation of a genetically modified (GM) plant into a sample or analyzing a mixing ratio. Here, the method includes incubating tissues of a GM plant or a non-GM plant, and separating a tissue-cultured cell line from the tissues.

Another aspect of the present invention provides a method of manufacturing a reference material for determining incorporation of a GM plant into a sample or analyzing a mixing ratio. Here, the method includes extracting genomic DNA from a tissue-cultured cell line which is obtained by incubating tissues of a GM plant or a non-GM plant.

Still another aspect of the present invention provides a method of determining incorporation of a GM plant. Here, the method includes designing primers specific to a base sequence of an inserted gene using a genomic DNA sample, which is extracted from a tissue-cultured cell line obtained by incubating tissues of a GM plant, as a template, and performing a polymerase chain reaction (PCR) on an analytic sample.

Yet another aspect of the present invention provides a method of analyzing a mixing ratio of a GM plant in a sample. Here, the method includes comparing genomic DNA samples, which are extracted from tissue-cultured cell lines obtained by incubating tissues of either a GM plant or a non-GM plant, with a PCR product, which is obtained from an analytic sample using a reference material for analyzing a mixing ratio of a GM plant.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which.

DETAILED DESCRIPTION OF EXEMPLARY EMBODIMENTS

Hereinafter, exemplary embodiments of the present invention will be described in detail. However, the present invention is not limited to the embodiments disclosed below, but can be implemented in various forms. The following embodiments are described in order to enable those of ordinary skill in the art to embody and practice the present invention.

Although the terms first, second, etc. may be used to describe various elements, these elements are not limited by these terms. These terms are only used to distinguish one element from another. For example, a first element could be termed a second element, and, similarly, a second element could be termed a first element, without departing from the scope of exemplary embodiments. The term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

The terminology used herein is for the purpose of describing particular embodiments only and is not intended to be limiting of exemplary embodiments. The singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, components and/or groups thereof, but do not preclude the presence or addition of one or more other features, integers, steps, operations, elements, components and/or groups thereof.

With reference to the appended drawings, exemplary embodiments of the present invention will be described in detail below.

The expression "mixing ratio of a GM plant in a sample" used herein means a value obtained by converting a ratio of an amount of a GM plant to the total amount of an unknown sample or a ratio of an endogenous gene and an artificially introduced modified gene of a certain crop into a percentage (%). The mixing ratio of the GM plant in the sample can be calculated using an inserted gene introduced into a GM plant or a protein expressed therefrom. That is, the percentage (%) of a relative amount of the GM plant can be determined by measuring a ratio of an amount or copy number of an inserted gene or a protein expressed therefrom to an endogenous gene or a protein expressed therefrom. The term "endogenous gene" means a gene that is inherently carried by each of crops, and the term "inserted gene" means an exogenous gene that is introduced into a GM plant.

Since the mixing ratio is calculated as described above, the purity of the starting sample used to manufacture a reference material affects all the quantitative results and provided a bias toward the quantitative results. Therefore, it is apparent that the purity of the starting sample used in the manufacture of a reference material serves as a highly important uncertainty factor. Despite the fact that the purity of a reference material is not secured since the reference material was manufactured using powder of seeds prior to the present invention, there is no practical way to solve the problem regarding the purity. This is because the purity of the starting sample cannot be verified since there is no alternative way to determine the purity except for a complete genetic survey of a seed and it is impossible to carry out the complete genetic survey in reality.

Therefore, the present invention aims to verify the purity of a starting sample used in the manufacture of a reference material as one method of verifying and securing the homogeneity of the starting sample using tissue-cultured cell lines, which are obtained by incubating tissues of a GM plant or a non-GM plant, or genomic DNA samples extracted therefrom as a reference material for determining incorporation of a GM plant into a sample or analyzing a mixing ratio. Since the use of the cell culturing technique makes it possible to produce a countless number of populations having the same genetic traits, it is possible to secure the homogeneity and purity of the starting sample with no quality variation between batches in the manufacture of the reference material.

The present invention is directed to providing a method of manufacturing a reference material for analyzing a mixing ratio of a GM plant in a sample, which includes incubating tissues of either a GM plant or a non-GM plant, and separating tissue-cultured cell lines from the tissues.

The term "reference material" used herein refers to a sample that functions as a standard to determine introduction of a GM plant or measure a mixing ratio. In this case, the reference material may mean a sample composed of either a 100% GM plant or a 100% non-GM plant, or a sample in which a GM plant is already present at a predetermined mixing ratio.

For the reference material for determining incorporation of a GM plant into a sample or analyzing a mixing ratio according to one exemplary embodiment of the present invention, tissue-cultured cell lines themselves of pure GM or non-GM plants, which are obtained by incubating certain tissues of a GM plant or non-GM plant, may be used as the 100% GMO or the 100% non-GMO reference material. In this case, the present invention is not limited to the tissue-cultured cell line of the GM plant or the non-GM plant. For example, the tissue-cultured cell line can be stored or distributed after pretreatment such as lyophilization.

The tissue-cultured cell line of a pure GM plant or non-GM plant itself, which is obtained by incubating the certain tissues of the GM plant or non-GM plant, may be used in a pure form. However, the tissue-cultured cell lines may be mixed at a predetermined ratio, and the resulting cell line sample may be manufactured as a reference material having a known GMO mixing ratio. The mixing ratio of a GM plant in an analytic sample may be readily analyzed by manufacturing a reference material having a known mixing ratio, amplifying the reference material using a real-time PCR to plot a standard curve and comparing the real-time PCR-amplified results of the analytic sample with the standard curve. Such a reference material may be, for example, manufactured so that the mixing ratio of each of the GM plants can amount to 0%, 0.1%, 0.5%, 1%, 2%, 3% or 5%, but the present invention is not limited thereto.

According to another exemplary embodiment of the present invention, the method of manufacturing a reference material for analyzing a mixing ratio of a GM plant in a sample may further include mixing the separated tissue-cultured cell lines of the GM plant or non-GM plant at a predetermined ratio. For example, the tissue-cultured cell lines of the GM plant or non-GM plant may be obtained by incubating certain tissues of the GM plant or non-GM plant, respectively, and the separated tissue-cultured cell lines of the GM plant and non-GM plant may be mixed at a predetermined ratio. Then, the resulting cell line sample may be used as the reference material having a known GMO mixing ratio. As will be described later, genomic DNA samples may be extracted from the tissue-cultured cell lines. Here, the genomic DNA samples may be used to determine incorporation of a GM plant into a sample or analyze a mixing ratio.

In addition, the present invention is directed to providing a method of manufacturing a reference material for analyzing a mixing ratio of a GM plant in a sample. Here, the method includes extracting genomic DNA from each of the tissue-cultured cell lines, which are obtained by incubating tissues of the GM plant or non-GM plant.

Genomic DNA samples extracted from the tissue-cultured cell lines of the GM plant or non-GM plant, which are obtained by incubating certain tissues of the GM plant or non-GM plant, respectively, that is, genomic DNA of the 100% GMO or 100% non-GMO, may be used as the reference material for determining incorporation of a GM plant into a sample or analyzing a mixing ratio analysis according to one exemplary embodiment of the present invention.

Each of the genomic DNA extracted from the tissue-cultured cell lines of the GM plant or non-GM plant itself may be used in a pure form. However, the tissue-cultured cell lines may be quantified and mixed at a predetermined ratio, and the resulting cell line sample may be manufactured as a reference material having a known GMO mixing ratio. The mixing ratio of a GM plant in an analytic sample may be readily analyzed by manufacturing a reference material having a known mixing ratio, amplifying the reference material using a real-time PCR to plot a standard curve and comparing the real-time PCR-amplified results of the analytic sample with the standard curve. Such a reference material may be, for example, manufactured so that the mixing ratio of each of the GM plants can amount to 0%, 0.1%, 0.5%, 1%, 2%, 3% or 5%, but the present invention is not limited thereto.

According to another exemplary embodiment of the present invention, the method of manufacturing a reference material for analyzing a mixing ratio of a GM plant in a sample may further include mixing the respective genomic DNA at a constant ratio. For example, each of the genomic DNA extracted from the tissue-cultured cell lines of the GM plant or non-GM plant, which are obtained by incubating certain tissues of the GM plant or non-GM plant, respectively, may be mixed at a predetermined ratio. Then, the resulting cell line sample may be used as the reference material.

The reference material most widely used so far is a standard plasmid that is constructed by inserting a powdery sample in which the GM plant and the non-GM plant are mixed at a constant ratio or an amplicon containing an endogenous gene and an inserted gene from the GM plant and the non-GM plant. In particular, since PCR amplicons of an endogenous gene and an inserted gene are inserted into the same plasmid, it is possible to endlessly supply a certain level of the standard plasmid as the reference material by growing the standard plasmid in *Escherichia coli* (*E. coli*). However, the use of the powdery reference material may cause the problems regarding the purity described above. When the standard plasmid is grown in *E. coli*, this is considered not to meet a strict definition of the term "reference material" according to the International Organization for Standardization (ISO) standard regarding the manufacture of a reference material. This is because two different samples (plant DNA and *E. coli* DNA) in which direct comparison of a medium effect referred to as a "matrix effect" is impossible are compared to each other. It is difficult to predict an effect of such a medium effect on the analytic results, but if it is difficult to predict the effect of the medium effect, it is recommended to use a reference material made of a similar medium. From this point of view, the reference material of genomic DNA derived from the plant according to the present invention may be more useful in preventing the erroneous results caused by the medium effect, compared to the plasmid DNA.

Furthermore, when the tissue-cultured cell lines themselves, which are obtained by incubating the tissues of the GM plant or non-GM plant, or the genomic DNA extracted therefrom are used to manufacture reference materials, a large amount of the reference materials having uniform qualities may be produced from a number of cultured cells having the same genetic traits, which are directly extracted from cells of the corresponding plant according to the present invention. Therefore, the constant and uniform supply of the reference material is possible, which makes it possible to analyze the mixing ratio of a GM plant in a sample more accurately, compared to a case of using a reference material whose purity is not reliably verified.

According to one exemplary embodiment of the present invention, the tissue culture according to the present invention may be carried out by incubating some of the certain tissues of the GM plant or non-GM plant in a liquid medium supplemented with proper nutrients and a plant growth regulator to produce a cultured cell line (callus) and subculturing the cultured cell line. The tissue culture may be performed under aseptic conditions.

In the present invention, a method of extracting DNA from the cultured cell line may be performed using any of methods known in the art. For example, DNA may be extracted using a method disclosed in "Method development in relation to regulatory requirements for the detection of GMOs in the food chain (Anklam et al. 2002, Journal of AOAC International. 85(3), 753)" or "Validation studies and proficiency testing (Anklam et al. 2002, Journal of AOAC International. 85(3), 809-815)," but the present invention is not limited thereto.

Also, the present invention is directed to providing a method of determining incorporation of a GM plant. Here, the method includes designing primers specific to a base sequence of an inserted gene using a genomic DNA sample, which is extracted from a tissue-cultured cell line obtained by incubating tissues of a GM plant, as a template and performing a PCR on an analytic sample. The incorporation of the GM plant containing an inserted gene may be qualitatively analyzed by determining whether a PCR product corresponding to the inserted gene is amplified from the analytic sample. Also, the incorporation of the GM plant may be qualitatively analyzed by comparing the PCR product of the analytic sample with the PCR product obtained using the GM plant or non-GM plant as a template.

In addition, the present invention is directed to providing a method of analyzing a mixing ratio of a GM plant in a sample. Here, the method includes comparing genomic DNA, which are extracted from tissue-cultured cell lines obtained by incubating tissues of a GM plant or a non-GM plant, with a PCR product, which is obtained from an analytic sample using a reference material for analyzing a mixing ratio of a GM plant.

According to one exemplary embodiment of the present invention, the comparison of the reference material with the PCR product obtained from the analytic sample may be performed using a real-time polymerase chain reaction (hereinafter referred to as a "real-time PCR"), but the present invention is not limited thereto.

Using the real-time PCR, amounts of endogenous and inserted genes may be calculated by measuring an intensity of fluorescence which is chromogenic in a PCR amplification procedure using a detection probe and bidirectional primers specifically binding to DNA of the endogenous gene and the inserted gene. This is a method of determining what percentage (%) of a GM plant is present in a sample from a relative ratio of the exogenous inserted gene to the endogenous gene which related plants essentially have in common.

In this case, the detection probe means a probe whose base sequence has a fluorescent material introduced therein so as to perform quantitative analysis in the real-time PCR. Kinds of the detection probe may be properly selected by those skilled in the art, depending on the kinds of the endogenous gene and the inserted gene.

According to one exemplary embodiment of the present invention, a standard curve representing the number of PCR cycles versus a gene copy number may be calculated by performing a real-time PCR on the reference material, using a detection probe, a primer for detecting an inserted gene and a primer for detecting an endogenous gene, to measure an intensity of fluorescence, and the mixing ratio of the GM plant in the sample may be analyzed by comparing the reference material with the real-time PCR product obtained from the analytic sample.

According to one exemplary embodiment of the present invention, the standard curve may be calculated by applying the number of PCR cycles versus a gene copy number, which is obtained by diluting a genomic DNA, which is extracted from a tissue-cultured cell line obtained by incubating tissues of the GM plant, at a predetermined ratio and performing real-time PCRs on a plurality of reference samples having different gene copy numbers.

According to another exemplary embodiment of the present invention, the standard curve may be calculated by applying the number of PCR cycles versus a gene copy number, which is obtained by mixing the genomic DNA, which are extracted from the tissue-cultured cell lines obtained by incubating tissues of the GM plant or the non-GM plant, at a predetermined ratio and performing PCRs on a plurality of reference samples having different gene copy numbers.

That is, several samples having constant copy numbers may be manufactured by properly diluting several reference materials having known mixing ratios of a GM plant in a sample with one reference material, or manufactured by mixing DNA of the GM plant and the non-GM plant at a predetermined ratio so that the samples can have constant mixing ratios. Then, when a real-time PCR is performed on the several samples, a level of fluorescence according to the number of PCR cycles may be measured. In this case, the number of PCR cycles at the time of increasing a fluorescence signal is referred to as a threshold cycle (Ct). In this case, this value refers to the most important value in the quantitative analysis using the real-time PCR at the time of establishing the most reproducible correlation with a starting concentration (gene copy number) of a sample. In the real-time PCR, the standard curve is plotted from the Ct value by applying a value obtained by converting a gene copy number of the reference material into a log value to the X axis and applying the number of PCR cycles versus the gene copy number to the Y axis. When the intensity of fluorescence of the analytic sample is applied to the standard curve, the gene copy number of the analytic sample may be calculated.

More particularly, according to one exemplary embodiment of the present invention, the mixing ratio of the GM plant in the sample may be measured more accurately using a conversion factor calculated by the following equation by applying the intensity of fluorescence, which is measured by performing a PCR on DNA of the 100% GM plant using a detection probe, a primer for detecting an inserted gene and a primer for detecting an endogenous gene, to the standard curve to measure a gene copy number. In general, the endogenous gene and the inserted gene are not innately present at the same copy number in the 100% GM plant. As a result, when the relative quantification is performed using the ratio of the endogenous gene and the inserted gene, a conversion factor (CO is used to correct parameters that can affect the ratio between the copy numbers of the endogenous gene and the inserted gene in the 100% GM plant and the PCR amplification efficiency in a DNA extraction procedure. The term "conversion factor" means a percentage of the DNA copy numbers between the inserted gene and the endogenous gene in one GM plant.

$$\text{Conversion Factor}(CF) = \frac{\text{Number of Inserted Genes in 100\% } GM \text{ plant}}{\text{Number of Endogenous Genes in 100\% } GM \text{ plant}}$$

However, since there are many species in one GM plant system and there are many species in one non-GM plant, the conversion factor may be affected according to the species used.

More particularly, according to one exemplary embodiment of the present invention, the mixing ratio of the GM plant in the sample may be measured by applying the intensity of fluorescence, which is measured by performing a PCR on the analytic sample using a detection probe, a primer for detecting an inserted gene and a primer for detecting an endogenous gene, to the standard curve. In particular, the mixing ratio of the GM plant in the sample may be measured according to the following equation used to calculate a mixing ratio.

$$\text{Mixing Ratio (\%)} = \frac{\text{Copy Number of Inserted Gene in Analytic Sample}}{\text{Copy Number of Endogenous Gene in Analytic Sample}} \times \frac{1}{\text{Conversion Factor}} \times 100$$

A method of quantitatively measuring the intensity of fluorescence using the real-time PCR is not particularly limited. For example, an SYBR Green I method, a Taqman probe method, a molecular beacon probe method or a hybridization probe method may be used as the method.

The SYBR Green I method is a method of measuring the intensity of fluorescence using a reagent, SYBR Green I, that binds to a minor groove of double-stranded DNA, which is a PCR product amplified by the PCR reaction, to emit fluorescence. Since the detected intensity of fluorescence is in proportion to an amount of amplified DNA, this may be a quantitative measurement means.

The Taqman probe method is a method of quantifying a level of innate fluorescence which is emitted by detaching a reporter fluorescent from the 5" terminus of a probe after the reporter fluorescent and a quencher are attached to the 5" terminus and 3" terminus of the probe, respectively, and a PCR is then performed. A base sequence of the probe is attached to only a base sequence of a target as a certain product, and the emission of the fluorescence is suppressed by the quencher bound to the 3" terminus of the probe when there is no PCR reaction. Since a level of fluorescence accumulatively increases in proportion to the PCR cycles, this may be a quantitative measurement means.

The molecular beacon probe method is a method of measuring the fluorescence. In a specific stem-and-loop structure (i.e., a hair-pin structure), a middle loop region has a base sequence complementary to a base sequence of a target and both of the termini have complementary base sequences of 4 to 7 base pairs, which bind to each other to form a stem structure. A reporter fluorescent is attached to the 5" terminus of the hair-pin structure, and a quencher, DABSYL, is attached to the 3" terminus of the hair-pin structure. As a result, when the hair-pin structure does not bind to the target in a structural aspect, the reporter fluorescent does not emit the fluorescence, whereas, when the hair-pin structure binds to the target, the loop region of the hair-pin structure attaches to a certain region of the PCR product amplified through the PCR, and the reporter fluorescent falling out of influence of the quencher emits the fluorescence while the hair-pin structure is disassembled.

The hybridization probe method is a method using two probes which are adjacent to each other in a base sequence of a target. In this case, a donor fluorescent is attached to the 3" terminus of one probe, and a receptor fluorescent is attached to the 5" terminus of the other probe. As a result, the fluorescence resonance energy transfer (FRET) takes place only when the probes lie adjacent to each other, and thus emission light of a donor may function as excitation light of a receptor. That is, the receptor fluorescent emits the fluorescence by means of energy transferred from the adjacent donor fluorescent. Here, since a level of fluorescence increases in proportion to an amount of the probe attached to the PCR product, this may be an indirectly quantitative measurement means.

Hereinafter, the present invention will be described with reference to Examples for better understanding of the present invention. However, it should be understood that the description proposed herein is merely a preferable example for the purpose of illustration only, and not intended to limit the scope of the invention. Therefore, the Examples of the present invention are provided to more completely explain the present invention to persons of ordinary skill in the art.

Example 1

Preparation of Tissue-Cultured Cell Line

Soybean from the US in which GM soybean (Glycine max) was mixed was randomly selected, germinated and grown. Thereafter, the gene analysis according to populations and tissues was performed to determine incorporation of the GM soybean.

Soybean was germinated in a dark room, and transferred and planted in the soil. Thereafter, when the soybean was grown in an incubator (dark/bright: 16/8 hours; 22/18° C., humidity of 80%) for a week, primary leaves formed. The leaves of this plant were collected, weighed, and then quenched in liquid nitrogen. Thereafter, genomic DNA was extracted, and subjected to gene amplification to determine whether the soybean was genetically modified.

The genetic modification of the soybean was determined by PCR amplifying a DNA fragment including a modified gene of GM soybean, that is, a gene (5-enolpyruvyl shikimate-3-phosphate synthase, EPSPS) resistant to a glyphosate-based herbicide. It was confirmed that a sample in which a band having the same size as the GM DNA was amplified was GM soybean, and a sample in which a band having the same size as the GM DNA was not amplified was non-GM soybean. Such a method was used to obtain the GM soybean or non-GM soybean suspension-cultured cell line and incubate and maintain the separated cell line. Since each of the cell lines was derived from one leaf, and then incubated and maintained in a separate vessel, there was no probability that one cell line was mixed or contaminated with another cell line. In this procedure, a GM soybean suspension-cultured cell line composed only of 100% GM cells and a non-GM soybean suspension-cultured cell line composed only of 100% non-GM cells were obtained.

A surface of each of leaves derived from the 100% GM soybean and the 100% non-GM soybean was sterilized with a bleach and 70% ethanol, and then grown in an LS (Linsmaier & Skoog) medium (excluding 6-benzylaminopurine; BAP) to induce formation of a callus. Then, the induced callus was incubated in another LS solid medium, or suspension-cultured in a liquid medium excluding Phytagel.

Composition of the LS medium was as follows: LS salt: 4.4 g/L, sucrose: 3% (30 g/L), BAP: 3 mg/mL, 2,4-dichlorophenoxy-acetic acid (2,4-D): 0.1 mg/ mL, and Phytagel: 0.3% (3 g/L).

The calluses on the solid medium were transferred to a new medium every third to fourth week, and the suspension-cultured cell lines were transferred to a new medium every tenth day. These culture conditions were 25° C. and a dark state, and the suspension-cultured cell lines were cultured while shaking at 200 rpm.

Figure 1:
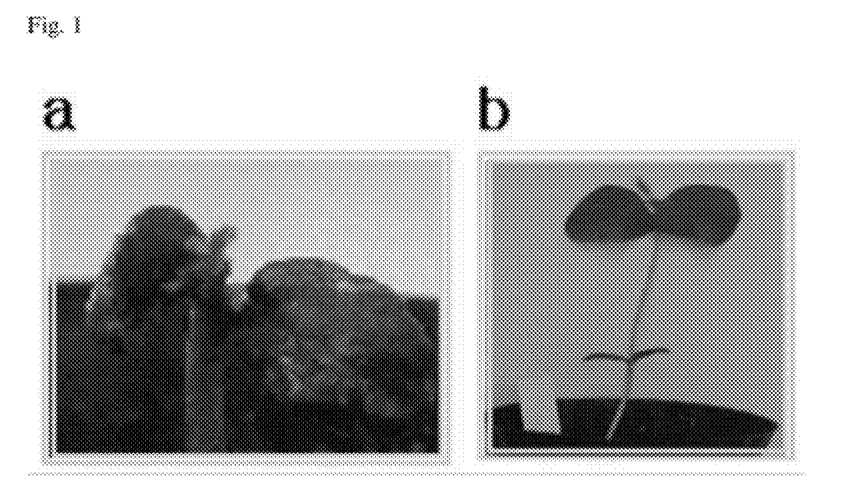
FIG. 1 shows (a) seed leaves of soybean formed 5 days after germination, and (b) a soybean plant having primary leaves 7 days after germination.

FIG. 1 shows (a) seed leaves of soybean formed 5 days after germination, and (b) a soybean plant having primary leaves 7 days after germination.

Figure 2:
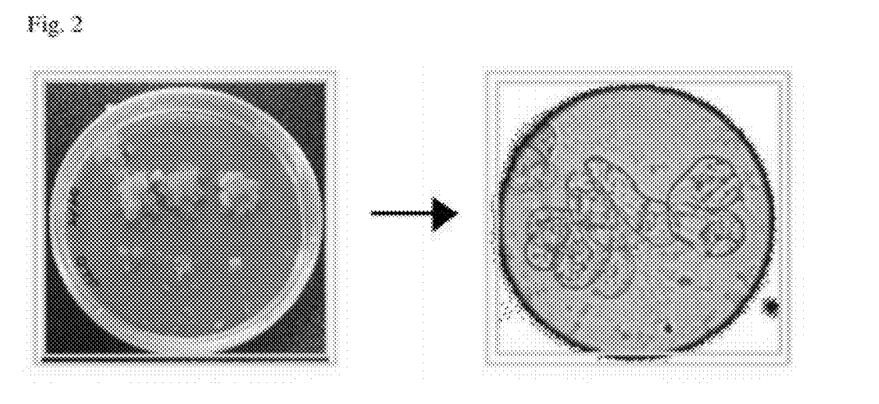
FIG. 2 shows a callus (left) derived from a leaf tissue of soybean and a cell microphotograph (right) of a liquid suspension-cultured cell line derived from the callus of soybean.

FIG. 2 shows a callus (left) derived from a leaf tissue of soybean and a cell microphotograph (right) of a liquid suspension-cultured cell line derived from the callus of soybean.

Figure 3:
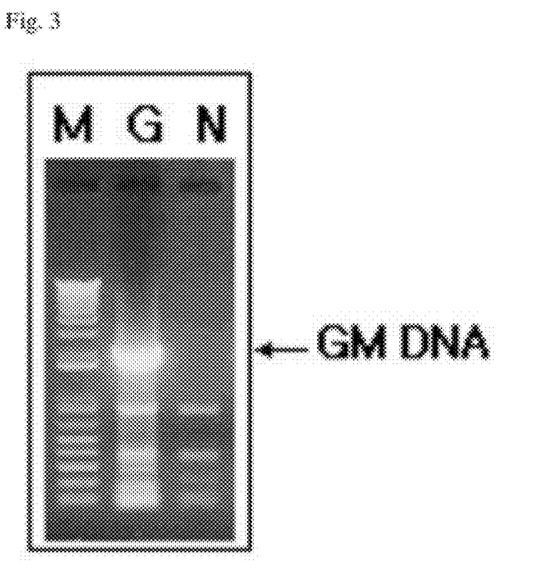
FIG. 3 shows the PCR results of an inserted gene using 35S3F and NOS3R PCR primers. (M: molecular marker DNA; G: GM soybean DNA; and N: non-GM soybean)

FIG. 3 shows that a sample in which a band having the same size along an arrow indicated by the GM DNA is amplified is GM soybean having an inserted gene, and a sample in which a band having the same size as the GM DNA is not amplified is non-GM soybean having no inserted gene.

Example 2

Extraction of Genomic DNA From Tissue-Cultured Cell Line

The extraction of genomic DNA was performed using a variety of widely used plant DNA extraction kits according to a method proposed by the manufacturer (Qiagen, Promega, etc.) or a slightly modified method, or using a modified method from a CTAB method, in which components were used at reduced amounts, as described in "Chapter 10. Tests on Gene-Recombinant Foods in General. Methods" of "Standards and Specifications in Foods" issued by the Korea Food and Drug Administration (KFDA).

Figure 4:
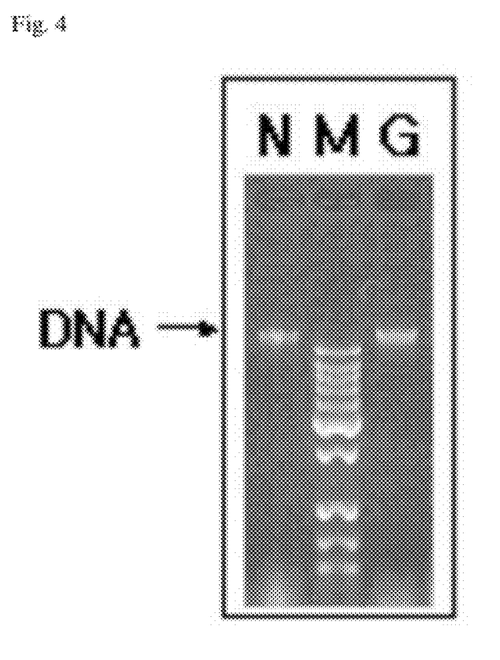
FIG. 4 shows the electrophoretic results of genomic DNA of soybean. (M: molecular marker DNA; G: GM soybean DNA; and N: non-GM soybean)

The extracted genomic DNA showed a pattern as shown in FIG. 4. The absorbance of the genomic DNA was measured under ultraviolet rays to confirm the purity, which was used later (see the KFDA's notification).

Experimental Example 1

Qualitative Analysis of Incorporation of GM Plant

The qualitative analysis was performed by PCR amplifying a DNA fragment including a modified gene of GM soybean, that is, a gene (i.e., EPSPS) resistant to a glyphosate-based herbicide.

The confirmation of the genetic modification of a sample through the gene amplification was performed according the method recommended by the KFDA or performed under the conditions as follows. When the genetic modification was confirmed under the following conditions, an amplified product had a size of approximately 2 kb. In addition, the genetic modification was confirmed using an endogenous gene, lectin, as the positive control.

In order to confirm the presence of an inserted gene, 2 µL of a forward primer 35S 3F (AAGATGCCTCTGCCGACA, 10 µM), 2 µL of a reverse primer NOS 3R (ATGTATAAT-TGCGGGACTCTAATCA, 10 µM), 2 µL of dNTP (10 mM), 2 µL of a 10× buffer, 2 µL of $MgCl_2$ (25 mM) and 0.2 µL of Taq polymerase (5 U/µL) were put into a PCR tube, approximately 50 ng of genomic DNA was added as the template DNA, and distilled water was added to give a total of 20 µL. The PCR reaction was performed in a gradient cycler PTC-0225 (MJ Research, Waltham, Mass.) under these conditions: one cycle of the denaturation step at 94° C. for 3 min; 35 cycles of the amplification step at 94° C. for 20 sec; at 60° C. for 30 sec; and at 72° C. for 2 min; and one cycle of the final elongation step at 72° C. for 10 min.

A lectin gene specific to soybean was used to confirm the presence of an endogenous gene. Here, this experiment was performed under the same conditions, except that only the following primers were used herein. Lec 3F (GACTA-GAGTGCTACAAATGCTTATC) and Lec 1R (GGCATA-GAAGGTGAAGTTGAAGGA) were used as the forward primer and the reverse primer, respectively.

FIG. 3 shows the PCR results of an inserted gene. In FIG. 3, a sample in which a band having the same size as the GM DNA was amplified was GM soybean having a modified gene, and a sample in which a band having the same size as the GM DNA was not amplified was non-GM soybean having no modified gene.

Figure 5:
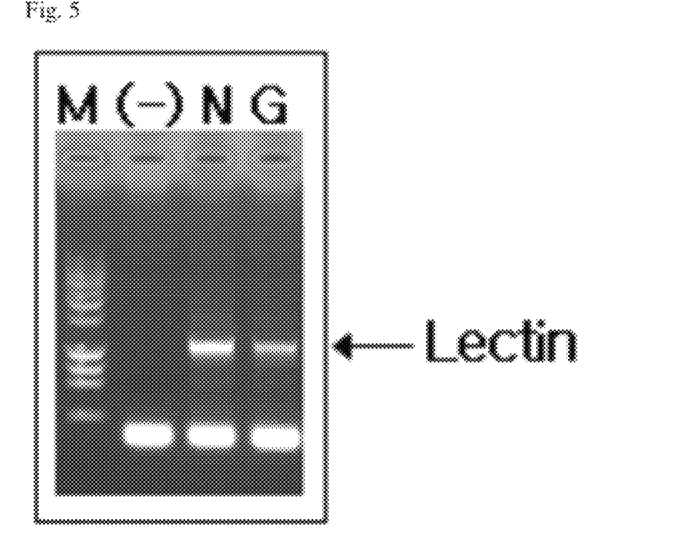
FIG. 5 shows the PCR results of an endogenous gene using Lec 3F and Lec 1R primers. (M: molecular marker DNA; G: GM soybean DNA; and N: non-GM soybean)

FIG. 5 shows the PCR results of an endogenous gene. In the case of the endogenous gene, the positive PCR results were obtained in both the GM plant and the non-GM plant.

Experimental Example 2

Verification of Purity of Genomic DNA Extracted From Tissue-Cultured Cell Line

In order to verify the purity of genomic DNA extracted from the tissue-cultured cell line of GM soybean according to the present invention, a real-time quantitative PCR was performed to quantitatively analyze a mixing ratio of a GM plant. Since a relative ratio of an endogenous gene to an inserted gene was calculated as described above so as to determine a mixing ratio of a GM plant in an analytic sample, a real-time PCR was used to confirm a level of gene amplification in real time. In this Experimental Example, all the experiments were performed using ABI 7900HT, and the basic designs of the experiments and components (i.e., primers, probes, etc.) of the experiments were used based on the data described in the KFDA's specifications.

First, the real-time quantitative PCR was performed using a widely used plasmid DNA (NipponGene, Japan) having a known copy number as a reference material to plot a standard curve, and using the genomic DNA, which was extracted from the tissue-cultured cell lines of the 100% GM soybeans prepared in Examples 1 and 2, as analytic samples.

Figure 6:
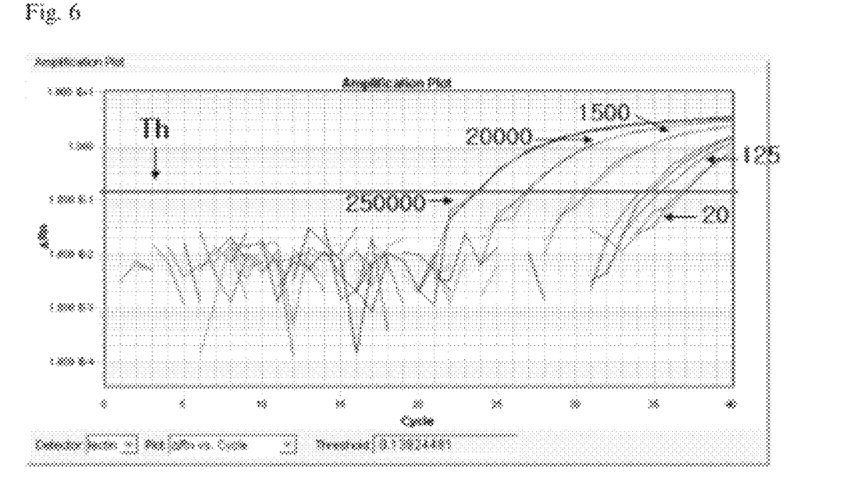
FIG. 6 is a diagram showing the results obtained by performing a real-time quantitative PCR using a widely used plasmid'DNA as the reference material.

FIG. 6 is a diagram showing the results obtained by amplifying an endogenous gene according to the concentrations of a widely used plasmid DNA having a known copy number used as the reference material. The plasmid DNA was added as the reference material so that the copy number could be in a range of 250,000 to 20 copies, thereby obtaining the reproducible results with the constant distances according to the concentrations. It could be seen that the same results tended to be obtained in the GM gene.

As a result, the genomic DNA extracted from the tissue-cultured cell line of the 100% GM soybean was used as the analytic sample to determine whether a GM relative quantitative value derived from the standard curve approached 100%.

Figure 7:
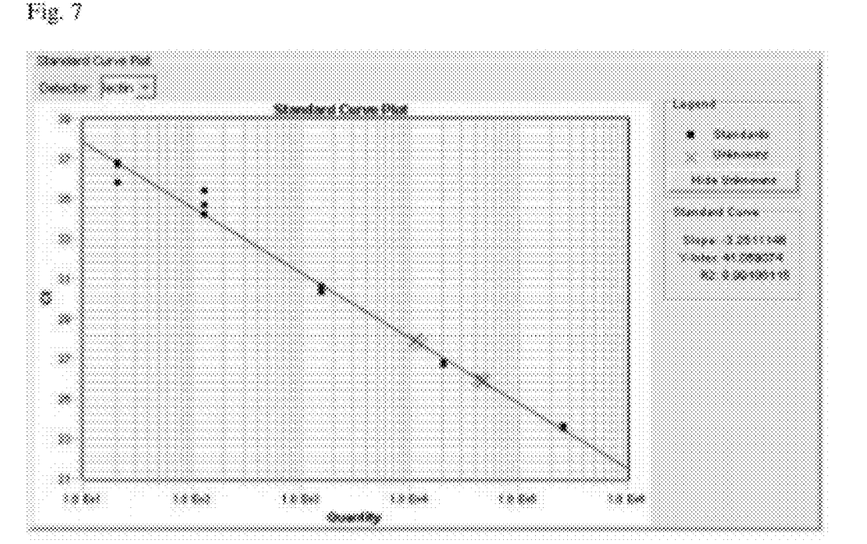
FIG. 7 is a diagram showing a standard curve plotted from the results obtained by performing the real-time quantitative PCR using the widely used plasmid DNA as the reference material.

FIG. 7 shows the experimental results showing a standard curve derived from the concentrations of DNA as shown in FIG. 6 and an amount of the endogenous gene (indicated by a red X) calculated from the standard curve. Here, the experiment was performed in triplicate. It was confirmed that the association of a regression line was 0.99 or more, and the GM mixing ratio was approximately 108%±2.6% (relative standard deviation), indicating highly precise results.

Next, the real-time quantitative PCR was performed in the same manner as described above using the plasmid DNA having a known copy number, which the inventors prepared themselves in the present invention, instead of the widely used plasmid reference material to plot a calibration curve, and using the genomic DNA, which was extracted from the tissue-cultured cell line of the 100% GM soybeans prepared in Examples 1 and 2, as the analytic sample.

Figure 8:
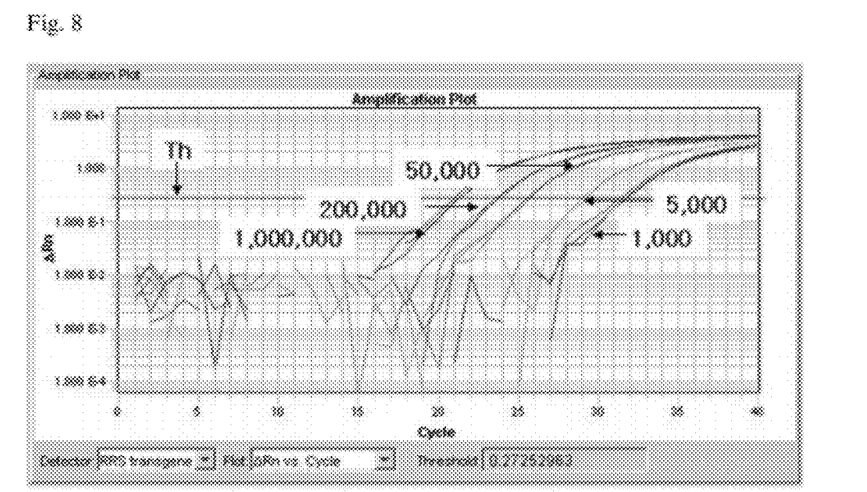
FIG. 8 is a diagram showing the results obtained by performing a real-time quantitative PCR using a plasmid DNA reference material manufactured according to the present invention.

FIG. 8 shows the results obtained by repeatedly performing the same experiment using the plasmid DNA having a known copy number, which the inventors prepared themselves in the present invention, as the reference material. The plasmid DNA was added as the reference material so that the copy number could be in a range of 1,000,000 to 1,000 copies, thereby obtaining the reproducible results with the constant distances according to the concentrations. It could be seen that the same results tended to be obtained in the endogenous gene.

As a result, the genomic DNA extracted from the tissue-cultured cell line of the 100% GM soybean was used as the analytic sample to determine whether a GM relative quantitative value derived from the standard curve approached 100%.

Figure 9:
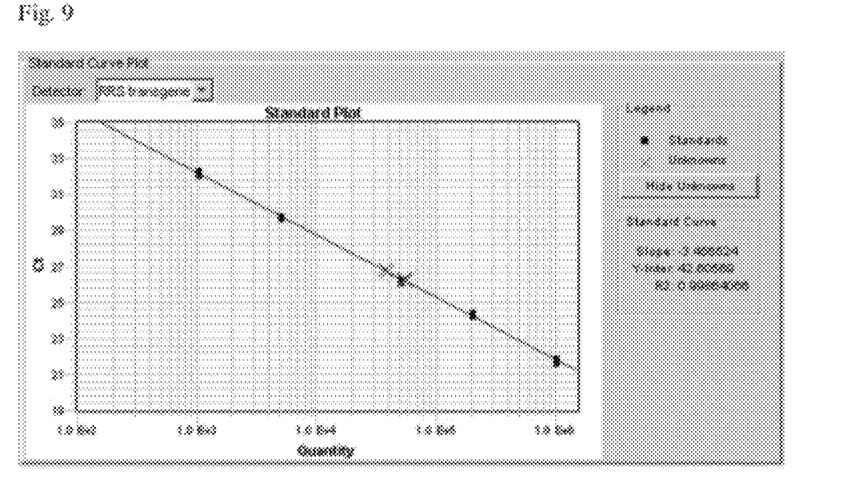
FIG. 9 is a diagram showing a standard curve plotted from the results obtained by performing the real-time quantitative PCR using the plasmid DNA reference material manufactured according to the present invention.

FIG. 9 shows the experimental results showing a standard curve derived from the concentrations of the DNA as shown in FIG. 8 and an amount of the GM gene (indicated by a red X) calculated from the standard curve. Here, the experiment was performed in triplicate. It was confirmed that the association of a regression line was 0.99 or more, and the GM mixing ratio was approximately 105%±5.5% (relative standard deviation), indicating highly precise results.

Experimental Example 3

Quantitative Analysis of Mixing Ratio of GM Plant in Analytic Sample Using Genomic DNA Extracted From Tissue-Cultured Cell Line as Reference Material In order to quantitatively analyze a mixing ratio of a GM plant, a real-time quantitative PCR was performed using the genomic DNA, which was extracted from the tissue-cultured cell line according to the present invention, as the reference material. The experimental method was performed in the same manner as in Experimental Example 2, except that the genomic DNA extracted from the tissue-cultured cell line whose GM relative quantitative value was proved to approach 100% in Experimental Example 2 was used as the reference material and a sample having a known GM mixing ratio (5% GM soybean ERM and IRMM-410S-5) was used as the analytic sample.

Figure 10:
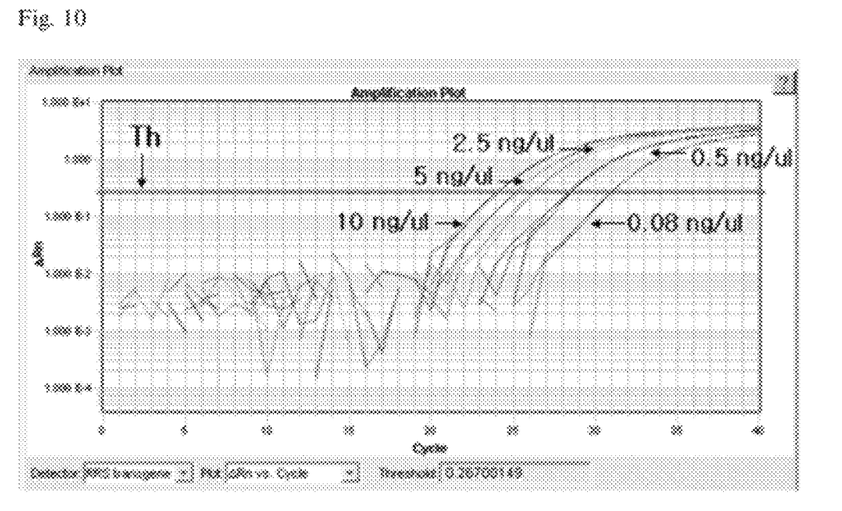
FIG. 10 is a diagram showing the results obtained by performing a real-time quantitative PCR using a genomic DNA reference material of a GM suspension-cultured cell line.

FIG. 10 shows the results obtained by amplifying an endogenous gene according to the concentrations of the genomic DNA extracted from the tissue-cultured cell line of the 100% GM soybean according to the present invention and used as the reference material. Here, the reproducible results were obtained by adding the genomic DNA at a DNA concentration of 10 ng/μL to 0.08 ng/$_μ$L.

Figure 11:
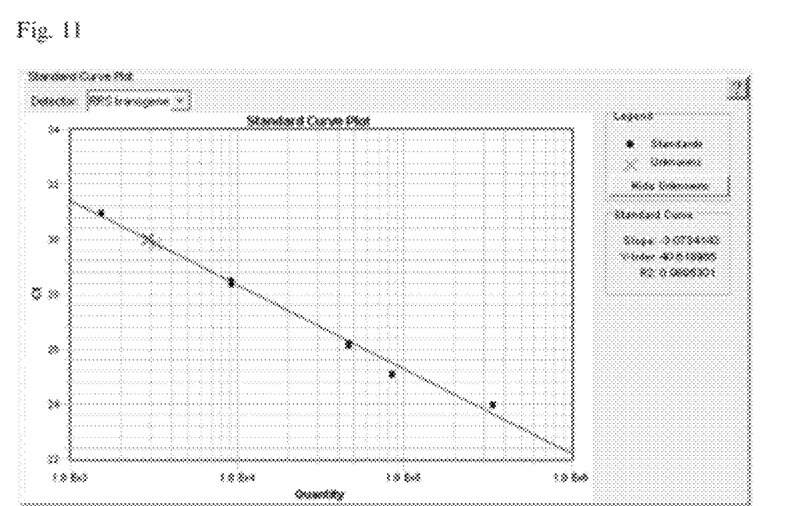
FIG. 11 is a diagram showing a standard curve plotted from the results obtained by performing the real-time quantitative PCR using the genomic DNA reference material of the GM suspension-cultured cell line.

FIG. 11 shows the experimental results showing a standard curve derived from the concentrations of the genomic DNA as shown in FIG. 10 and an amount of the GM gene (indicated by a red X) calculated from the standard curve. Here, the experiment was performed in triplicate. As a result, it was confirmed that the association of a regression line was approximately 0.99. Even when a verified value of the corresponding ERM was slightly different from 4.76% ±0.47% (relative standard deviation), the GM mixing ratio (%) was shown to be approximately 4%, which was relatively proximate to the verified value. When the experiment was performed in various concentrations, a mixing ratio more approximate to the verified value was expected to be obtained.

Experimental Example 4

Calculation of Conversion Factor

Since a GM plant had an inserted gene having different copy numbers, it was necessary to correct the relationship with the endogenous gene according to respective GM plants. The conversion factor used to determine a mixing ratio of a GM plant was calculated by performing a real-time quantitative PCR. The real-time quantitative PCR was performed using the widely used plasmid DNA having a known copy number (NipponGene, Japan) and the plasmid DNA having a known copy number, which the inventors prepared themselves in the present invention, as the reference materials to plot a standard curve, and using the genomic DNA, which was extracted from the suspension-cultured cell lines of the 100% GM soybean prepared in Examples 1 and 2, as the analytic sample, a primer for detecting an inserted gene and a primer for detecting an endogenous gene. The endogenous gene used to calculate the conversion factor was a lectin gene specific to soybean, and Le1n02-5" (GCCCTC-TACTCCACCCCA) and Le1n02-3" (GCCCATCTG-CAAGCCTTTTT) were used as the forward and reverse primers for detecting an endogenous gene, respectively. Le1-Taq (FAM-AGCTTCGCCGCTTCCTTCAACTTCAC-TAMRA) was used as the detection probe. The inserted gene was an RRS gene, and RRS01-5" (CCTTTAGGATTTCA-GCATCAGTGG) and RRS01-3" (GACTTGTCGC-CGGGAATG) were used as the forward and reverse primers for detecting an inserted gene, respectively. Also, RRS-Taq (FAM-CGCAACCGCCCGCAAATCC-TAMRA) was used as the detection probe.

The conversion factor was calculated according to the following equation after the copy numbers of the inserted gene and the endogenous gene in the analytic sample were calculated from the standard curve of the reference material.

$$\text{Conversion Factor}(CF) = \frac{\text{Number of Inserted Genes in 100\% } GM \text{ plant}}{\text{Number of Endogenous Genes in 100\% } GM \text{ plant}}$$

Table 1 lists the results of the conversion factor calculated using the plasmid DNA having a known copy number (NipponGene, Japan) as the reference material. Here, the conversion factor was shown to be 1.08.

TABLE 1

| | Mean value | Standard deviation | Relative standard deviation |
|---|---|---|---|
| GM soybean | 1.08 | 0.03 | 2.63 |

Table 2 lists the results of the conversion factor calculated using the plasmid DNA having a known copy number, which the inventors prepared themselves in the present invention, as the reference material. Here, the conversion factor was shown to be 1.05.

TABLE 2

| | Mean value | Standard deviation | Relative standard deviation |
|---|---|---|---|
| GM soybean | 1.05 | 0.06 | 5.52 |

Experimental Example 5

Determination of Mixing Ratio of GM Plant in Analytic Sample by Application of Conversion Factor In order to quantitatively analyze a mixing ratio of a GM plant, the real-time quantitative PCR was performed using the widely used plasmid DNA having a known copy number (NipponGene, Japan) and the plasmid DNA having a known copy number, which the inventors prepared themselves in the present invention, as the reference materials to plot a standard curve, and using the genomic DNA, which was extracted from the suspension-cultured cell line of the 100% GM soybean, as the analytic sample. The copy numbers of the inserted gene and the endogenous gene in the analytic sample were calculated from the standard curve of the two reference materials, and the conversion factor calculated in Experimental Example 4 was then applied thereto to determine the GM mixing ratio. In this case, it was confirmed that the GM mixing ratio approached 100%. The equation used to determine a GM mixing ratio by application of the conversion factor was as follows.

$$\text{Mixing Ratio (\%)} = \frac{\text{Copy Number of Inserted Gene in Analytic Sample}}{\text{Copy Number of Endogenous Gene in Analytic Sample}} \times \frac{1}{\text{Conversion Factor}} \times 100$$

Table 3 lists the results of the GM mixing ratio determined by applying a conversion factor of 1.08 calculated in Experimental Example 4 using the widely used plasmid DNA having a known copy number (NipponGene, Japan) as the reference material. It was confirmed that the GM mixing ratio was approximately 100.03% and thus the GM relative quantitative value nearly approached 100%.

TABLE 3

$$\begin{aligned}\text{Mixing Ratio (\%)} &= \frac{\text{Copy Number of Inserted Gene in Analytic Sample}}{\text{Copy Number of Endogenous Gene in Analytic Sample}} \times \frac{1}{\text{Conversion Factor}} \times 100 \\ &= \frac{51315.7}{47314.2} \times \frac{1}{1.08} \times 100 \\ &= 100.03\%\end{aligned}$$

Table 4 lists the results of the GM mixing ratio determined by applying a conversion factor of 1.05 calculated in Experimental Example 4 using the plasmid DNA having a known copy number, which the inventors prepared themselves in the present invention, as the reference material. It was confirmed that the GM mixing ratio was approximately 99.8% and thus the GM relative quantitative value nearly approached 100%.

TABLE 4

$$\begin{aligned}\text{Mixing Ratio (\%)} &= \frac{\text{Copy Number of Inserted Gene in Analytic Sample}}{\text{Copy Number of Endogenous Gene in Analytic Sample}} \times \frac{1}{\text{Conversion Factor}} \times 100 \\ &= \frac{347107.3}{332307.9} \times \frac{1}{1.05} \times 100 \\ &= 99.8\%\end{aligned}$$

According to the present invention, the reference material for determining incorporation of a genetically modified (GM) plant into a sample or analyzing a mixing ratio using the tissue-cultured cell lines which are obtained by incubating tissues of a GM plant or a non-GM plant can be useful in producing a countless number of populations having the same genetic traits via the tissue culture. Thus, when a culture capacity of the reference material is increased to a large volume, it is possible to obtain a large volume of the reference material having uniform qualities with no quality variation between batches. Unlike the conventional reference materials manufactured using grain powder, a GM or non-GM reference material with 100% purity can also be obtained by verifying the purity of the tissue-cultured cell line. Accordingly, it is possible to provide the uniform and stable supply of a reference material having uniform composition.

While the invention has been shown and described with reference to certain exemplary embodiments thereof, it will be understood by those skilled in the art that various changes in form and details may be made therein without departing from the scope of the invention as defined by the appended claims.

What is claimed is:

1. A method for determining the proportion of GM material in a testing sample of a subject plant, comprising:
   manufacturing a genomic DNA reference material;
   performing real-time PCR on the genomic DNA reference material and the testing sample using a detection probe and a primer for detecting the inserted GM gene, and a detection probe and a primer for detecting an endogenous gene, and measuring the fluorescence during DNA amplification;
   preparing a standard curve by plotting the number of PCR cycles versus a gene copy number for the genomic DNA reference material; and
   performing a comparison of the genomic DNA reference material and the testing sample by using the standard curve, whereby the proportion of GM material in the subject plant is determined,
   wherein the step of manufacturing the genomic DNA reference material comprises the following steps:
   establishing tissue cultured cell lines of a 100% GM or a 100% non-GM plant;
   separating tissue-cultured cell lines from the tissues, respectively;
   incubating and maintaining the separated tissue-cultured cell lines; and
   extracting the genomic DNA samples from the incubated tissue-cultured cell lines of the 100% GM plant, the 100% non-GM plant, or a mixture thereof.

2. The method of claim 1, wherein the standard curve is calculated by applying the number of PCR cycles versus a gene copy number, which is obtained by mixing the genomic DNA samples, which are extracted from the tissue-cultured cell lines obtained by incubating tissues of the GM plant or the non-GM plant, at a predetermined ratio and performing PCRs on a plurality of reference samples having different gene copy numbers.

3. The method of claim 1, wherein the comparison of the reference material with the real-time PCR product obtained from the analytic sample comprises:
   calculating a conversion factor according to the following equation by applying a fluorescence intensity, which is measured by performing a PCR on DNA of a 100% GM plant using a detection probe, a primer for detecting an inserted gene and a primer for detecting an endogenous gene, to the standard curve to measure a gene copy number:

$$\text{Conversion Factor}(CF) = \frac{\text{Number of Inserted Genes in 100\% } GM \text{ plant}}{\text{Number of Endogenous Genes in 100\% } GM \text{ plant}}$$

4. The method of claim 1, wherein the mixing ratio of the GM plant in the sample is measured using the gene copy number which is calculated by applying the fluorescence intensity, which is measured by performing PCRs on the analytic sample using a detection probe, a primer for detecting an inserted gene and a primer for detecting an endogenous gene, to the standard curve.

5. The method of claim 4, wherein the mixing ratio of the GM plant in the sample is measured using the following equation used to calculate a mixing ratio:

$$\text{Mixing Ratio (\%)} = \frac{\text{Copy Number of Inserted Gene in Analytic Sample}}{\text{Copy Number of Endogenous Gene in Analytic Sample}} \times \frac{1}{\text{Conversion Factor}} \times 100$$

* * * * *